United States Patent
Seidel et al.

(10) Patent No.: US 9,785,058 B2
(45) Date of Patent: Oct. 10, 2017

(54) METHOD FOR ASCERTAINING DISTORTION PROPERTIES OF AN OPTICAL SYSTEM IN A MEASUREMENT SYSTEM FOR MICROLITHOGRAPHY

(71) Applicant: Carl Zeiss SMT GmbH, Oberkochen (DE)

(72) Inventors: Dirk Seidel, Jena-Leutra (DE); Susanne Toepfer, Etzleben (DE); Michael Himmelhaus, Jena (DE)

(73) Assignee: Carl Zeiss SMT GmbH, Oberkochen (DE)

( * ) Notice: Subject to any disclaimer, the term of this patent is extended or adjusted under 35 U.S.C. 154(b) by 129 days.

(21) Appl. No.: 14/825,343

(22) Filed: Aug. 13, 2015

(65) Prior Publication Data
US 2015/0346608 A1 Dec. 3, 2015

Related U.S. Application Data

(63) Continuation of application No. PCT/EP2014/052776, filed on Feb. 13, 2014.
(Continued)

(30) Foreign Application Priority Data

Feb. 14, 2013 (DE) .................. 10 2013 101 445

(51) Int. Cl.
*G03F 7/20* (2006.01)
*G01B 11/02* (2006.01)
(Continued)

(52) U.S. Cl.
CPC .......... *G03F 7/70433* (2013.01); *G01B 11/02* (2013.01); *G03F 1/84* (2013.01);
(Continued)

(58) Field of Classification Search
CPC .... G03F 1/84; G03F 7/70433; G03F 7/70616; G03F 7/70625
See application file for complete search history.

(56) References Cited

U.S. PATENT DOCUMENTS

| 5,818,572 | A | * | 10/1998 | Pappas | ............... | G01M 11/0292 |
|           |   |   |         |        |                | 356/124.5    |
| 7,831,105 | B2 |  | 11/2010 | Engel et al. | | |

(Continued)

FOREIGN PATENT DOCUMENTS

| DE | 103 27 019 | 12/2004 | ............ G01M 11/02 |
| DE | 10 2006 030 670 | 1/2008 | ............... G06T 5/00 |

(Continued)

OTHER PUBLICATIONS

Längle et al., "Pattern Placement Metrology Using PROVE™ High Precision Optics combined with Advanced Correction Algorithms", Optical Measurement Systems for Industrial Inspection VII, Proc. of SPIE, vol. 8082, No. 1, pp. 80820J-1-80820J-12 (May 23, 2011).

(Continued)

*Primary Examiner* — Michelle M Iacoletti
(74) *Attorney, Agent, or Firm* — Fish & Richardson P.C.

(57) ABSTRACT

A method for ascertaining distortion properties of an optical system in a measurement system for microlithography is provided, wherein the optical system images at least one structure to be measured into a measurement image. In accordance with one aspect, a method according to the invention comprises the following steps: measuring the field-dependent image aberrations of the optical system; determining a first distortion pattern present in the first image field generated by the optical system during measurement of at least one predefined structure; carrying out an optical forward simulation for the predefined structure taking account of the field-dependent image aberrations measured previously, with a second image field being generated; determining a second distortion pattern for the second image field generated previously; and ascertaining the structure-independent distortion properties of the optical system by calculating a third distortion pattern as the difference (Continued)

between the first distortion pattern and the second distortion pattern.

10 Claims, 5 Drawing Sheets

Related U.S. Application Data

(60) Provisional application No. 61/764,815, filed on Feb. 14, 2013.

(51) Int. Cl.
*G03F 1/84* (2012.01)
*G01N 21/956* (2006.01)

(52) U.S. Cl.
CPC .............. *G03F 7/705* (2013.01); *G03F 7/706* (2013.01); *G03F 7/70425* (2013.01); *G03F 7/70483* (2013.01); *G03F 7/70525* (2013.01); *G03F 7/70616* (2013.01); *G03F 7/70625* (2013.01); *G03F 7/70666* (2013.01); *G01N 2021/95676* (2013.01)

(56) References Cited

U.S. PATENT DOCUMENTS

| | | | | |
|---|---|---|---|---|
| 2002/0001088 | A1* | 1/2002 | Wegmann | G01J 9/02 356/521 |
| 2002/0183332 | A1 | 12/2002 | D'Alche-Biree | |
| 2006/0007429 | A1* | 1/2006 | Emer | G01J 9/00 356/124 |
| 2010/0104128 | A1 | 4/2010 | Arnz et al. | |
| 2010/0208935 | A1 | 8/2010 | Arnz et al. | |
| 2010/0246993 | A1* | 9/2010 | Rieger | G06T 5/006 382/275 |
| 2012/0063666 | A1 | 3/2012 | Arnz et al. | |
| 2012/0314910 | A1 | 12/2012 | Arnz | |

FOREIGN PATENT DOCUMENTS

| | | | | |
|---|---|---|---|---|
| DE | 10 2006 059 431 | | 6/2008 | ............... G03F 7/20 |
| DE | 10 2007 033 815 | | 11/2008 | ............... G03F 9/00 |
| DE | 10 2010 045 135 | | 3/2012 | ............... G03F 9/00 |
| WO | WO 01/12265 | | 2/2001 | ............... A61P 25/30 |

OTHER PUBLICATIONS

International Search Report and Written Opinion of the International Searching Authority for International Application No. PCT/EP2014/052776 dated Jun. 23, 2014 (15 pages).
International Preliminary Report on Patentability and Written Opinion of the International Searching Authority for International Application No. PCT/EP2014/052776 dated Aug. 27, 2015 (9 pages).
German Office Action for German Application No. 10 2013 101 445.3 dated Jan. 16, 2014 (11 pages).

* cited by examiner

METHOD FOR ASCERTAINING DISTORTION PROPERTIES OF AN OPTICAL SYSTEM IN A MEASUREMENT SYSTEM FOR MICROLITHOGRAPHY

CROSS REFERENCE TO RELATED APPLICATIONS

This application is a continuation of PCT application PCT/EP2014/052776, filed on Feb. 13, 2014, which claims priority to German patent application DE 10 2013 101 445.3 and U.S. provisional patent application 61/764,815, both filed on Feb. 14, 2013. The entire contents of the above applications are herein incorporated by reference.

BACKGROUND OF THE INVENTION

Field of the Invention

The invention relates to a method for ascertaining distortion properties of an optical system in a measurement system for microlithography.

Prior Art

Microlithography is used for producing microstructured components, such as integrated circuits or LCDs, for example. The microlithography process is carried out in a so-called projection exposure apparatus comprising an illumination device and a projection lens. The image of a mask (also referred to as a reticle) illuminated by the illumination device is in this case projected by the projection lens onto a substrate (e.g., a silicon wafer) coated with a light-sensitive layer (photoresist) and arranged in the image plane of the projection lens, in order to transfer the mask structure to the light-sensitive coating of the substrate.

A characterization of the structures on the mask is performed both with regard to present deviations of the respective structure on the mask from the desired position predefined by the design (so-called positioning error or "registration error") and with regard to the linewidth of the structures (CD="critical dimension").

For determining the positioning error, various methods are known in the prior art.

By way of example, a "threshold-based" image evaluation can be applied to the structures of the aerial image, as is known from US 2012/0063666 A1.

Alternatively, by using a position measurement system, a first aerial image of a segment of the mask can be recorded and compared with a simulated second aerial image, whereupon the positioning error is then equated with the distance between the structures to be measured in the measured first aerial image and the simulated second aerial image. When ascertaining the second aerial image by simulation, effects within the optical beam path of the position measurement system (e.g., on account of the numerical aperture of the position measurement system, proximity effects, etc.) are taken into account, and the inclusion of all optical parameters of the system in the generation of the simulated aerial image during the image comparison yields a result which is to the greatest possible extent independent of said optical parameters (such that the measurement result is independent of the measurement system). Such a method (which sometimes is also designated as "die-to-database" comparison where "die" refers to the measurement image and "database" refers to the simulated image) makes it possible, owing to taking account of effects in the optical beam path, to increase the accuracy in relation to a comparison of the measured aerial image with a (direct) design image of the mask.

One problem that occurs in practice, however, is that the measurement image is deformed or distorted on account of the properties of the optical system (that is to say that a coordinate grid is not exactly at right angles on the measurement image), whereas the simulated image as an ideal simulated grid does not have this property.

One known approach for taking account of the distortion consists in the latter being calibrated or "extracted computationally", i.e. the distortion being determined metrologically by a targeted measurement with test structures in the image field. In this case, however, the further problem occurs that the distortion taken as a basis in such a calibration is dependent on the type of structure used for calibration and, consequently, is no longer exactly valid for any other possible structures.

With regard to the prior art, reference is made for example to WO 2001/012265 A1, DE 10 2007 033 815 A1 and DE 10 2006 059 431 A1, US 2010/0104128 A1, DE 10 2007 033 815 A1 and also the publication M. Längle et al.: "Pattern placement metrology using PROVE high precision optics combined with advanced correction algorithms," Proc. SPIE 8082, 80820J (2011).

SUMMARY OF THE INVENTION

In a general aspect, the present invention provides a method for ascertaining distortion properties of an optical system in a measurement system for microlithography which enables a more accurate specification of the distortion properties depending on the structure to be measured.

A method for ascertaining distortion properties of an optical system, in particular of a measurement system or inspection system for microlithography, wherein the optical system generates an image field during measurement of at least one structure, comprises the following steps:

measuring the field-dependent image aberrations of the optical system;

determining a first distortion pattern present in the first image field generated by the optical system during measurement of at least one predefined structure;

carrying out an optical forward simulation for the predefined structure taking account of the field-dependent image aberrations measured previously, with a second image field being generated;

determining a second distortion pattern for the second image field generated previously; and ascertaining the structure-independent distortion properties of the optical system by calculating a third distortion pattern as the difference between the first distortion pattern and the second distortion pattern.

The invention proceeds firstly from the consideration that the distortion that occurs during measurement of at least one structure in the generated image field has two components, of which one is independent of the currently measured structure type, whereas the other is dependent on the structure type.

Figure 5:
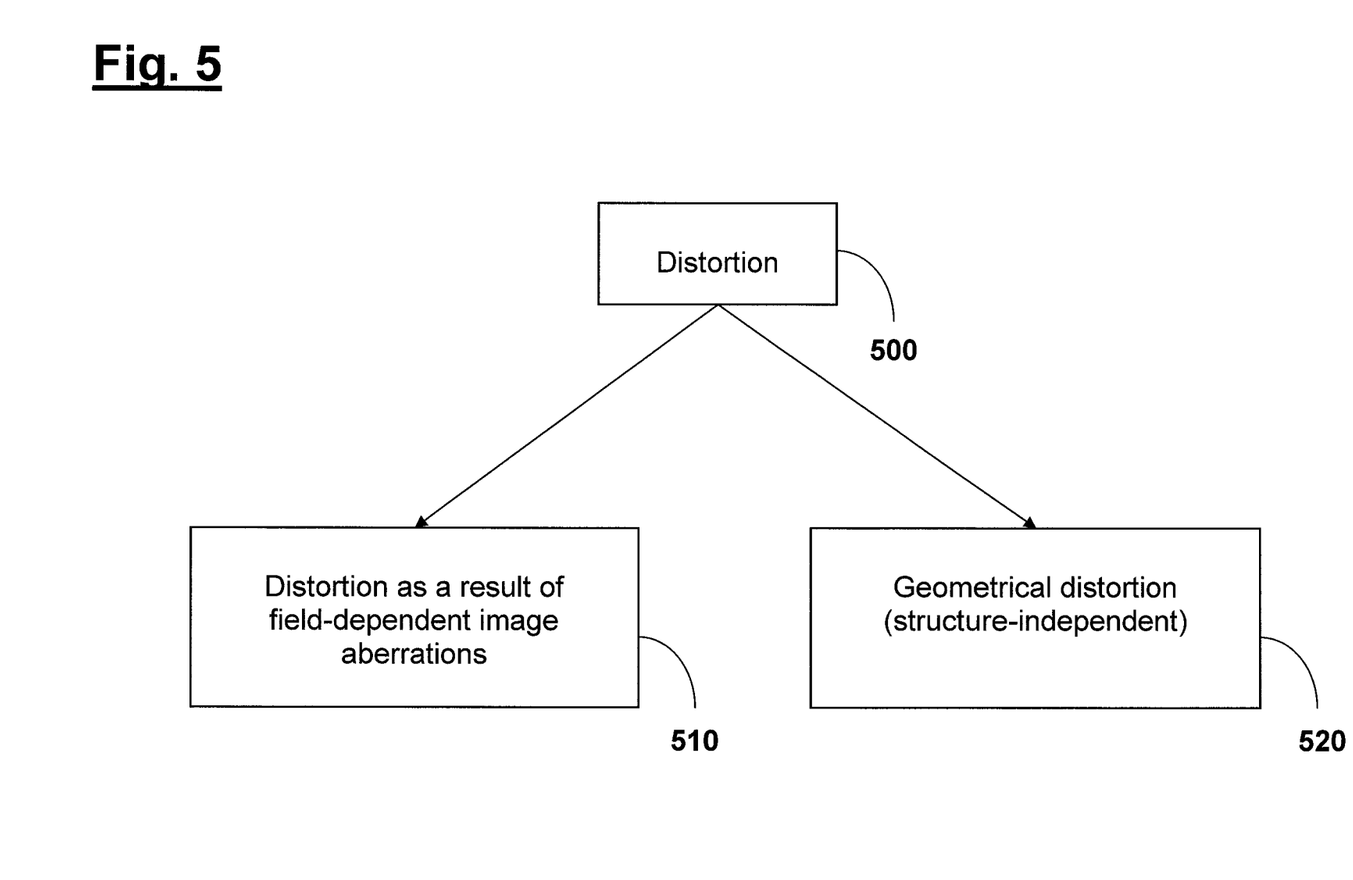
FIG. 5 shows a schematic illustration for elucidating the principle underlying the present invention.

This is illustrated schematically in FIG. 5, wherein the total distortion that occurs in the measured image is designated by "500". In this case, the image aberrations 520 that are independent of the structure type are those which result from so-called geometrical distortion effects (for example owing to inhomogeneities or stress birefringence in the material of the optical components or on account of alignment errors, camera tilts, camera cover glass stresses, etc.). By contrast, the image aberrations 510 that are dependent on the structure type result from the fact that the optical system has image aberrations (such as, e.g., coma or astigmatism)

which are dependent on the field position of the structure (since the beams pass differently through the optical assembly and thus have field-dependent image aberrations). These field-dependent image aberrations lead to a structure-dependent deformation of the image field.

Proceeding from this consideration, the invention is then based on the concept of separating the geometrical distortion effects or image aberrations 520 that are independent of the structure type from the image aberrations 510 that are dependent on the structure type, or separating them from one another in the calibration in such a way that the correct distortion can be taken into account or compensated for during each measurement.

In particular, the invention makes it possible that, e.g., during a subsequently carried out image comparison (e.g., for ascertaining registration errors), the images to be compared (namely measurement image and simulated image) correspond or are "made to coincide" with regard to distortion effects, which can be achieved either by the distortion being extracted computationally from the measurement image or by the distortion being "introduced" or "added computationally" to the simulated image (that is to say that either the measurement image is rectified or the simulated image is deformed). In this case, the invention comprises the concept of carrying out this rectification or deformation in a structure-dependent manner. To put it more precisely, in accordance with FIG. 5, the total distortion 500 is divided into the component 510 (=distortion on account of field-dependent image aberrations) and the component 520 (=geometrical distortion), wherein the structure-independent portion 520 can be used in each case uniformly for deformation or rectification, whereas for the structure-dependent component 510 (on account of the field-dependent image aberrations of the optical system) the currently "correct" component (i.e., the component associated with the relevant structure) is used in each case.

As a result, the invention enables the more accurate determination or specification of properties of an optical system to the effect that a correct separation or differentiation of field-dependent image aberrations and image aberrations on account of geometrical distortion is obtained.

In principle, the method according to the invention can advantageously be used in conjunction with an arbitrary optical system (e.g., a microscope) in which the separation of distortion effects of the imaging into an object-structure-dependent component (i.e., field-dependent image aberrations) and a geometrical component (i.e., object-structure- and illumination-independent image aberrations) is desired.

Said optical system can be, in particular, a system for determining the position of structures on a mask for microlithography, an inspection measurement system for measuring defects of photomasks, a system for determining the linewidth in photomasks, a phase measurement system for photomasks or an inspection system for localizing defects of photomasks.

The invention furthermore also relates to a method for determining the position of structures on a mask for microlithography, wherein the position determining is carried out on the basis of the comparison of a measurement image with a simulated image, said measurement image being generated by an optical system for a segment of the mask, wherein the method comprises the following steps:
ascertaining a structure-independent distortion pattern for the optical system; and
carrying out the image comparison between measurement image and simulated image taking account of this structure-independent distortion pattern.

Further configurations of the invention can be gathered from the description and from the dependent claims.

The invention is explained in greater detail below on the basis of exemplary embodiments illustrated in the accompanying figures.

DETAILED DESCRIPTION OF PREFERRED EMBODIMENTS

Figure 1:
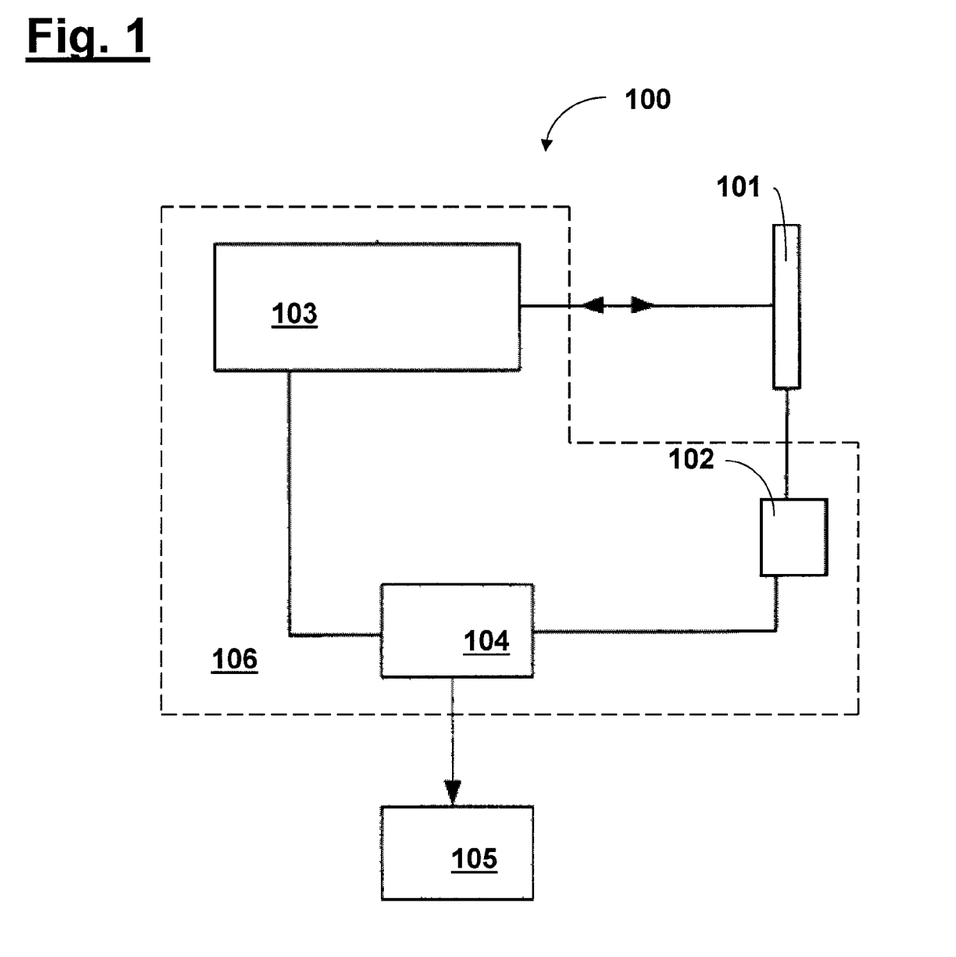
FIG. 1 shows a schematic illustration of the construction of a system for determining the position of structures on a mask as a possible application of the method according to the invention.

Firstly, for elucidating one possible application of the invention, the construction of a position measurement system suitable for determining the measured aerial image is described below with reference to the schematic illustration in FIG. 1. The position measurement system 100 in accordance with FIG. 1 comprises a recording device 106 having a positioning device 102 serving for setting the position of a lithography mask 101, an optical system 103, by which segments of the lithography mask 101 can be recorded in a magnified fashion, and also a control device 104. The position measurement system 100 in accordance with FIG. 1 furthermore comprises an evaluation device 105. The image data of the recordings generated by the recording device 106 are fed to the control device 104, which forwards the data to the evaluation device 105. By using the position measurement system 100, a measurement image (in the form of a first aerial image) of a segment of the lithography mask 101 is recorded and compared with a simulated second (aerial) image, whereupon the positioning error is then equated with the distance between the measurement image and the simulated image.

A method according to the invention will now be described below with reference to FIG. 2 et seq., which method, by using suitable calibration, achieves the effect that the images (namely measurement image and simulated image) to be compared during the image comparison carried out (e.g., for ascertaining registration errors), even taking account of the structures specifically measured in each case, correspond with regard to distortion effects, that is to say in other words that structure-dependent distortion effects or image aberrations can be taken into account correctly in each case.

The method according to the invention aims here to separate the structure-dependent from the geometrical (structure-independent) distortion effects, as explained below on the basis of one preferred embodiment with reference to the flow chart shown in FIG. 2.

A first step S210 involves carrying out firstly, in a manner known per se, a measurement of the field-dependent image aberrations in the image field of the optical system on a grid R (this method known as such is sometimes also designated as "phase retrieval").

The next step S220 involves carrying out a measurement of a first distortion pattern, which represents the total distortion $V_{tot}$ of the image field of the optical system 103, on the same grid R, e.g., by using a self-calibration on the basis of a structure or else a periodic array of structures which is moved around in a first image field generated during the measurement of the structures. This step S220 is also carried out in a manner known per se, wherein reference is made to the prior art known from the publication M. Längle et al.: "Pattern placement metrology using PROVE high precision optics combined with advanced correction algorithms", Proc. SPIE 8082, 80820J (2011).

The further step S230 involves carrying out, for the same structure for which the measurement of the first distortion pattern or of the total distortion $V_{tot}$ of the image field from step S220 was carried out, an optical forward simulation with generation of a second image field, wherein the field-dependent image aberrations which were ascertained in step S210 are taken into account. In this case, therefore, to an extent only that component of the distortion pattern which is caused by the field-dependent image aberrations (component 510 in FIG. 5) is simulated. In other words, in this simulation ultimately a separation is achieved to the effect that during the simulation only the component 510 (of the field-dependent image aberrations) from FIG. 5 is "added," such that a distortion pattern is obtained which "contains within itself" said component 510.

The next step S240 involves carrying out the determination of a second distortion pattern for the second image field obtained from the preceding step S230, which is in turn carried out by the method already employed in step S220 and known from the abovementioned publication M. Längle et al.: "Pattern placement metrology . . . " The distortion pattern obtained in this case can be designated as "simulated distortion" $V_{sim}$ and contains only the effects of the field-dependent image aberrations, but not geometrical distortion effects (e.g. camera tilts, camera cover glass stresses, etc.).

The distortion pattern $V_{sim}$ is a function of the field-dependent image aberrations. If the latter are represented in the customary basis as Zernike parameters $Z_k$, then $V_{sim} = V_{sim}(Z_k)$ therefore holds true. Since the field-dependent image aberrations $Z_k$ can also change over time, it is furthermore advantageous according to the invention also to determine in step S240 the change $W_k$ in the distortion pattern $V_{sim}$ in the event of a change in the Zernike parameters by an absolute value $\Delta Z_k$:

$$V_{sim} = V_{sim}(Z_k) \quad (1)$$
$$= V_{sim}(Z_k^{(0)} + \Delta Z_k)$$
$$= V_{sim}(Z_k^{(0)}) + \Sigma(\partial V_{sim}/\partial Z_k)\Delta Z_k$$
$$= V_{sim}(Z_k^{(0)}) + \Sigma W_k \Delta Z_k$$

Therefore, the changed distortion pattern can be calculated directly from the change in the field-dependent image aberrations $Z_k$. If the dependence of the simulated distortion pattern on the field-dependent image aberrations is stored as a model, $V_{sim}$ can also easily be corrected in the event of a change in the field-dependent image aberrations, without once again carrying out the entire step S230 and/or S240.

The next step S250 involves calculating the distortion difference from the first and second distortion patterns $$V_{indep} = V_{tot} - V_{sim} \quad (2)$$

The (third) distortion pattern $V_{indep}$ obtained in this case contains only distortion effects which do not result from field-dependent image aberrations, that is to say represents the geometrical distortion present uniformly (i.e., structure-independently).

Figure 2:
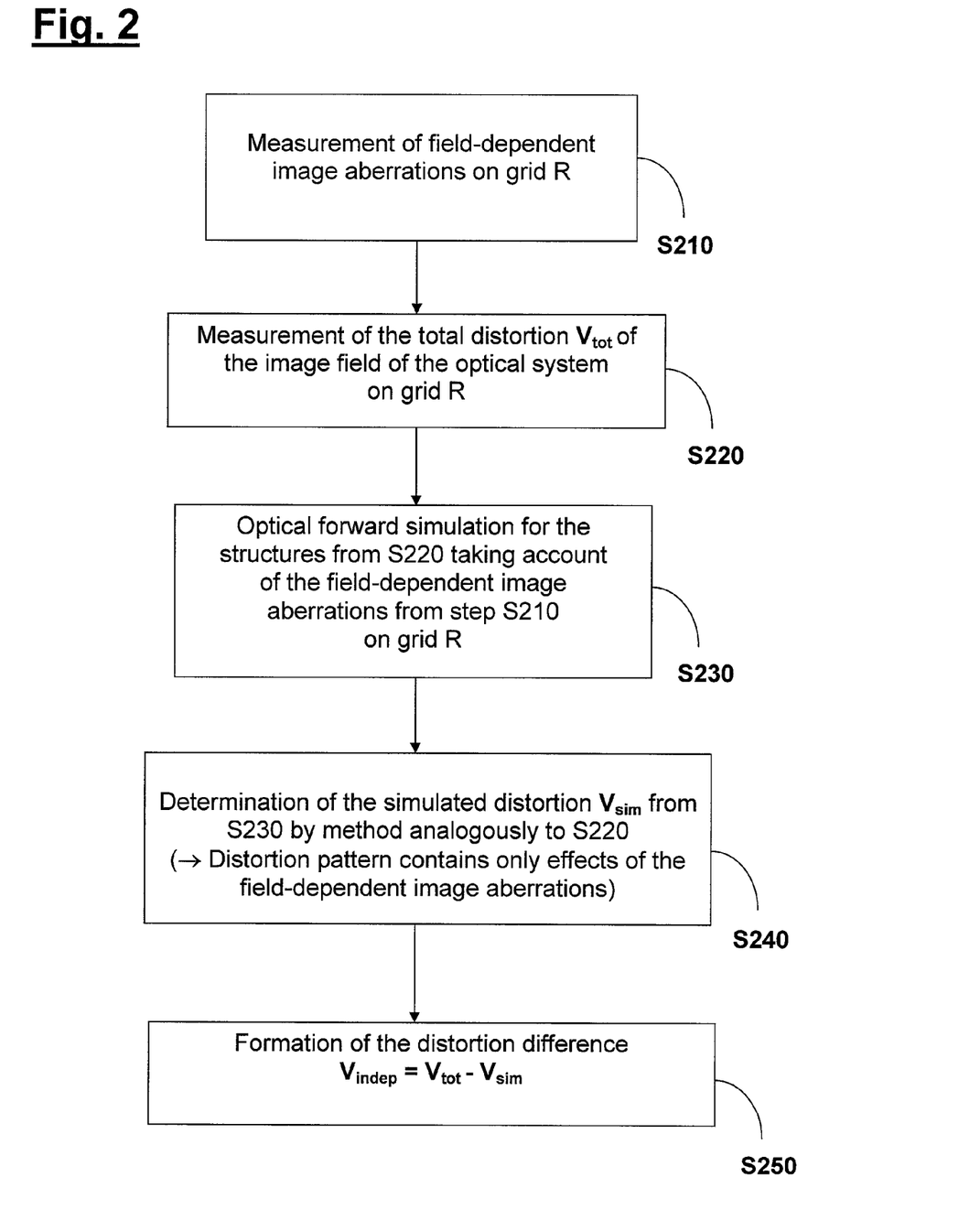
FIG. 2 shows a schematic illustration for elucidating one embodiment of the method according to the invention.

On the basis of the result obtained with the method from FIG. 2, it is then possible, for example, in any further simulation of an arbitrary structure, in each case to correctly include the structure-dependent distortion. This can be carried out for example by the method illustrated in the flow chart in FIG. 3.

Figure 3:
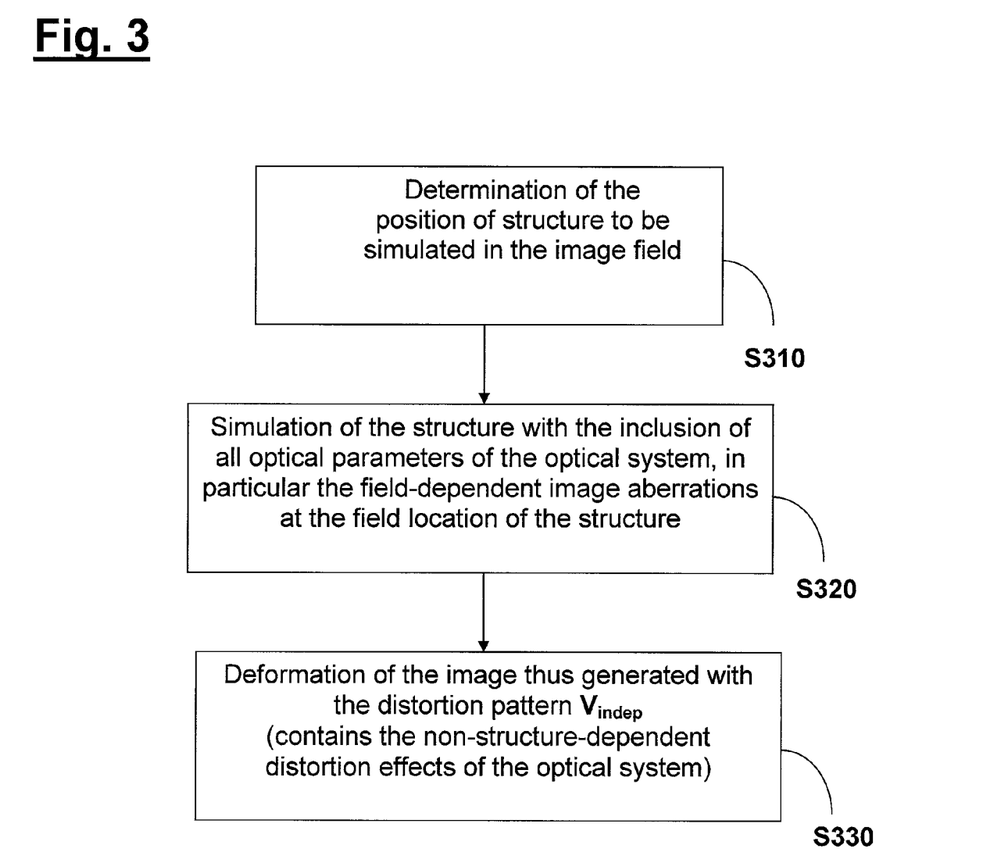
FIGS. 3-4 show flow charts for elucidating further configurations or applications of the method according to the invention.

In accordance with FIG. 3, step S310 involves carrying out firstly a determination of the position of the structure to be simulated in the image field. The next step S320 then involves carrying out a simulation of said structure with the inclusion of all optical parameters of the optical system (that is to say, in particular, including the field-dependent image aberrations at the field location of the structure), as a result of which a simulated image is obtained which, however, must now be correspondingly conditioned before the image comparison with the measurement image is carried out, said image comparison serving for position determination, wherein the results ascertained by the above-described method with regard to the distortion effects are taken into account.

Step S330 involves carrying out for this purpose a deformation of the simulated image generated in step S320 with the distortion pattern $V_{indep}$ described above in accordance with the method in FIG. 2 (which distortion pattern contains only the structure-independent distortion effects of the optical system). The resulting simulated image then corresponds very well (i.e., in particular both with regard to the effects as a result of field-dependent image aberrations and with regard to the effects as a result of the other distortion of the optical system) to a measurement image of the optical system.

Figure 4:
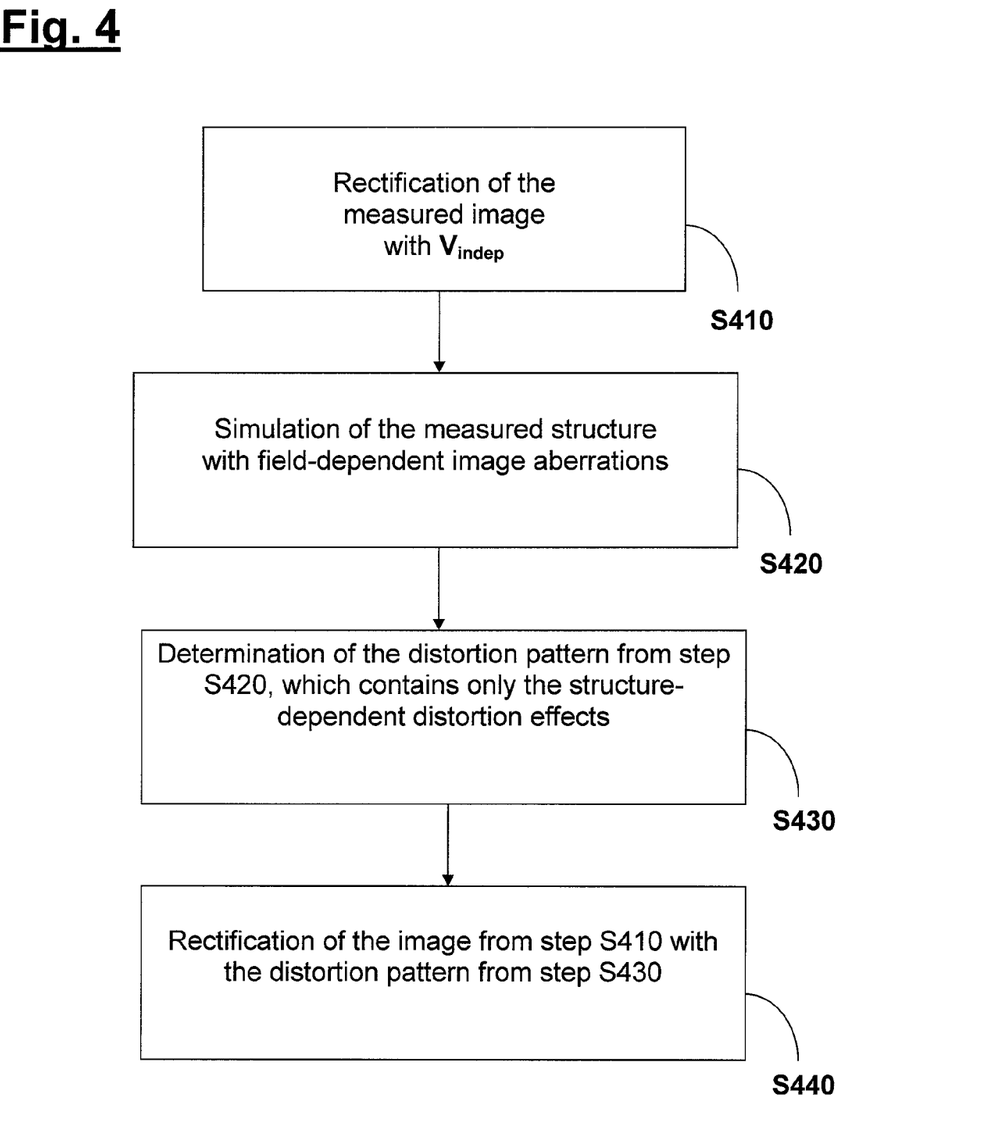

The correct inclusion of both the structure-dependent and the structure-independent distortion, this inclusion being made possible according to the invention, can furthermore also be carried out by the method illustrated in the flow chart in FIG. 4.

Step S410 involves carrying out firstly a rectification of the image measured by the position measurement system 100 or the optical system 103 with the distortion pattern $V_{indep}$ described above in accordance with the method in FIG. 2 (which distortion pattern contains the structure-independent distortion effects of the optical system). A simulation of the measured structure with field-dependent image aberrations is then carried out in step S420.

The next step S430 involves carrying out a determination of the distortion pattern from step S420 (which contains only the structure-dependent distortion effects). Step S440 then involves carrying out a rectification of the image from step S410 with the distortion pattern from step S430. As a result, this method involves carrying out in the measurement image a rectification both with regard to the structure-dependent image aberrations and with regard to the structure-independent image aberrations. In the image rectified in this way, the so-called "threshold method", as is known from US 2012/0063666 A1, can be employed for determining the position of the structure.

Even though the invention has been described on the basis of specific embodiments, numerous variations and alternative embodiments are evident to a person skilled in the art, e.g., by combination and/or exchange of features of individual embodiments. Accordingly, it goes without saying for a person skilled in the art that such variations and alternative embodiments are concomitantly encompassed by the present invention, and the scope of the invention is restricted only within the meaning of the accompanying patent claims and the equivalents thereof.

What is claimed is:

1. A method for ascertaining distortion properties of an optical system in a measurement system for microlithography, wherein the optical system images at least one structure to be measured into a measurement image, the method comprising the following steps:
   a) measuring the field-dependent image aberrations of the optical system;
   b) determining a first distortion pattern present in a first image field generated by the optical system during measurement of at least one predefined structure;
   c) carrying out an optical forward simulation for the predefined structure taking account of the field-dependent image aberrations measured in step a), with a second image field being generated;
   d) determining a second distortion pattern for the second image field generated in step c); and
   e) ascertaining the structure-independent distortion properties of the optical system by calculating a third distortion pattern as the difference between the first distortion pattern and the second distortion pattern.

2. The method according to claim 1, wherein on the basis of the third distortion pattern during an image comparison subsequently carried out between a measurement image and a simulated image, these images are made to coincide with regard to distortion effects.

3. The method according to claim 1, wherein the measurement system comprises at least one of a system for determining the position of structures on a mask for microlithography, an inspection measurement system for measuring defects of photomasks, a system for determining the linewidth in photomasks, a phase measurement system for photomasks or an inspection system for localizing defects of photomasks.

4. A method for determining the position of structures on a mask for microlithography, wherein the position determining is carried out on the basis of the comparison of a measurement image with a simulated image, said measurement image being generated by an optical system for a segment of the mask, the method comprising the following steps:
   ascertaining a distortion pattern brought about by structure-independent distortion properties of the optical system; and
   carrying out the image comparison between measurement image and simulated image taking account of this distortion pattern;
   wherein carrying out the image comparison between the measurement image and the simulated image comprises deforming the simulated image with the distortion pattern brought about by structure-independent distortion properties of the optical system.

5. The method according to claim 4, wherein ascertaining the distortion pattern brought about by structure-independent distortion properties of the optical system is carried out by a method comprising the following steps:
   a) measuring the field-dependent image aberrations of the optical system;
   b) determining a first distortion pattern present in the first image field generated by the optical system during measurement of at least one predefined structure;
   c) carrying out an optical forward simulation for the predefined structure taking account of the field-dependent image aberrations measured in step a), with a second image field being generated;
   d) determining a second distortion pattern for the second image field generated in step c); and
   e) ascertaining the structure-independent distortion properties of the optical system by calculating a third distortion pattern as the difference between the first distortion pattern and the second distortion pattern.

6. The method according to claim 5 in which on the basis of the third distortion pattern during an image comparison subsequently carried out between a measurement image and a simulated image, these images are made to coincide with regard to distortion effects.

7. The method according to claim 6 in which the measurement system comprises at least one of a system for determining the position of structures on a mask for microlithography, an inspection measurement system for measuring defects of photomasks, a system for determining the linewidth in photomasks, a phase measurement system for photomasks or an inspection system for localizing defects of photomasks.

8. The method according to claim 6, wherein carrying out the image comparison between measurement image and simulated image furthermore comprises the following steps:
   i. rectifying the measurement image taking account of the distortion pattern brought about by structure-independent distortion properties of the optical system;
   ii. carrying out an optical forward simulation for the structures on the mask taking account of the field-dependent image aberrations;
   iii. determining a structure-dependent distortion pattern for an image field generated during said forward simulation; and
   iv. rectifying the image obtained in step i with the distortion pattern generated in step iii.

9. The method according to claim 7, wherein carrying out the image comparison between measurement image and simulated image furthermore comprises the following steps:
   i. rectifying the measurement image taking account of the distortion pattern brought about by structure-independent distortion properties of the optical system;
   ii. carrying out an optical forward simulation for the structures on the mask taking account of the field-dependent image aberrations;
   iii. determining a structure-dependent distortion pattern for an image field generated during said forward simulation; and
   iv. rectifying the image obtained in step i. with the distortion pattern generated in step iii.

10. The method according to claim 5, wherein carrying out the image comparison between measurement image and simulated image furthermore comprises the following steps:
   i. rectifying the measurement image taking account of the distortion pattern brought about by structure-independent distortion properties of the optical system;
   ii. carrying out an optical forward simulation for the structures on the mask taking account of the field-dependent image aberrations;
   iii. determining a structure-dependent distortion pattern for an image field generated during said forward simulation; and
   iv. rectifying the image obtained in step i. with the distortion pattern generated in step iii.

* * * * *